United States Patent
Shelton, IV et al.

(10) Patent No.: US 11,957,336 B2
(45) Date of Patent: Apr. 16, 2024

(54) PROXIMALLY LOCATED FIRING LOCKOUT MECHANISM FOR SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Adam D. Hensel, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/402,703

(22) Filed: Aug. 16, 2021

(65) Prior Publication Data
US 2023/0051105 A1   Feb. 16, 2023

(51) Int. Cl.
| | |
|---|---|
| *A61B 17/068* | (2006.01) |
| *A61B 17/072* | (2006.01) |
| *A61B 34/30* | (2016.01) |

(52) U.S. Cl.
CPC ........ *A61B 17/0686* (2013.01); *A61B 17/072* (2013.01); *A61B 34/30* (2016.02);
(Continued)

(58) Field of Classification Search
CPC ............................................ A61B 2017/07285
(Continued)

(56) References Cited

U.S. PATENT DOCUMENTS

| | | | |
|---|---|---|---|
| 5,129,570 A | 7/1992 | Schulze et al. | |
| 6,010,054 A | * 1/2000 | Johnson | ........... A61B 17/07207 227/176.1 |

(Continued)

FOREIGN PATENT DOCUMENTS

| | | |
|---|---|---|
| EP | 3235444 A2 | 10/2017 |
| EP | 3338678 A2 | 6/2018 |

(Continued)

OTHER PUBLICATIONS

U.S. Appl. No. 17/088,941, entitled "Surgical Stapler End Effector Sled Having Cartridge Wall Support Feature," filed Nov. 4, 2020.
(Continued)

*Primary Examiner* — Thanh K Truong
*Assistant Examiner* — Patrick B Fry
(74) *Attorney, Agent, or Firm* — Frost Brown Todd LLP

(57) ABSTRACT

A surgical instrument includes a shaft assembly, an end effector, a firing system, and a firing lockout assembly. The end effector is operatively coupled with the shaft assembly. The end effector includes first and second jaws. The first jaw includes an anvil. The second jaw is configured to removably receive an unspent staple cartridge. The firing system extends through at least a portion of the shaft assembly and the end effector. The firing lockout assembly is selectively coupled with the firing system. The firing lockout assembly is disposed proximal to the end effector. The firing lockout assembly is configured to allow actuation of the firing system in an unlocked configuration in response to the unspent staple cartridge being coupled with the second jaw; and inhibit actuation of the firing system in a locked configuration in response to the unspent staple cartridge being absent from the second jaw.

19 Claims, 14 Drawing Sheets

(52) U.S. Cl.
CPC ............... *A61B 2017/07257* (2013.01); *A61B 2017/07271* (2013.01); *A61B 2017/07285* (2013.01)

(58) Field of Classification Search
USPC ...................................................... 227/175.4
See application file for complete search history.

(56) References Cited

U.S. PATENT DOCUMENTS

| | | | |
|---|---|---|---|
| 7,404,508 | B2 | 7/2008 | Smith et al. |
| 7,434,715 | B2 | 10/2008 | Shelton, IV et al. |
| 7,644,848 | B2* | 1/2010 | Swayze ................... A61B 34/76 227/19 |
| 7,721,930 | B2 | 5/2010 | McKenna et al. |
| 7,810,692 | B2 | 10/2010 | Hall et al. |
| 7,832,408 | B2 | 11/2010 | Shelton, IV et al. |
| 7,845,537 | B2 | 12/2010 | Shelton, IV et al. |
| 8,083,120 | B2 | 12/2011 | Shelton, IV et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 8,708,213 | B2 | 4/2014 | Shelton, IV et al. |
| 9,060,770 | B2 | 6/2015 | Shelton, IV et al. |
| 9,186,142 | B2 | 11/2015 | Fanelli et al. |
| 9,517,065 | B2 | 12/2016 | Simms et al. |
| 9,622,746 | B2 | 4/2017 | Simms et al. |
| 9,717,497 | B2 | 8/2017 | Zerkle et al. |
| 9,717,498 | B2* | 8/2017 | Aranyi ............. A61B 17/07207 |
| 9,795,379 | B2 | 10/2017 | Leimbach et al. |
| 9,808,248 | B2 | 11/2017 | Hoffman |
| 9,839,487 | B2 | 12/2017 | Dachs, II |
| 10,011,018 | B2 | 7/2018 | McGrogan et al. |
| 10,092,292 | B2 | 10/2018 | Boudreaux et al. |
| 10,206,678 | B2* | 2/2019 | Shelton, IV ..... A61B 17/07207 |
| 10,307,170 | B2 | 6/2019 | Parfett et al. |
| 10,485,621 | B2 | 11/2019 | Morrissette et al. |
| 10,537,400 | B2 | 1/2020 | Dachs, II et al. |
| 10,610,313 | B2 | 4/2020 | Bailey et al. |
| 10,639,034 | B2* | 5/2020 | Harris ............. A61B 17/07207 |
| 10,667,809 | B2 | 6/2020 | Bakos et al. |
| 10,806,530 | B2 | 10/2020 | Liao et al. |
| 10,863,988 | B2 | 12/2020 | Patel et al. |
| 10,881,401 | B2* | 1/2021 | Baber ................... A61B 90/03 |
| 11,020,138 | B2 | 6/2021 | Ragosta |
| 11,026,755 | B2 | 6/2021 | Weir et al. |
| 11,076,926 | B2 | 8/2021 | Ragosta et al. |
| 11,147,552 | B2 | 10/2021 | Burbank et al. |
| 11,166,773 | B2 | 11/2021 | Ragosta et al. |
| 11,234,700 | B2 | 2/2022 | Ragosta et al. |
| 11,259,884 | B2 | 3/2022 | Burbank |
| 11,517,312 | B2* | 12/2022 | Wixey ............... A61B 17/2841 |
| 2006/0185682 | A1 | 8/2006 | Marczyk |
| 2012/0209314 | A1 | 8/2012 | Weir et al. |
| 2015/0297228 | A1 | 10/2015 | Huitema et al. |
| 2016/0361126 | A1 | 12/2016 | Schena et al. |
| 2017/0020617 | A1 | 1/2017 | Weir et al. |
| 2017/0196558 | A1* | 7/2017 | Morgan ................. A61B 34/30 |
| 2017/0265865 | A1 | 9/2017 | Burbank |
| 2017/0265954 | A1 | 9/2017 | Burbank et al. |
| 2017/0333037 | A1 | 11/2017 | Wellman et al. |
| 2018/0168756 | A1 | 6/2018 | Liao et al. |
| 2018/0271608 | A1 | 9/2018 | Ragosta et al. |
| 2018/0310935 | A1 | 11/2018 | Wixey |
| 2018/0325606 | A1 | 11/2018 | Weir et al. |
| 2018/0344419 | A1 | 12/2018 | Dachs, II et al. |
| 2019/0038371 | A1 | 2/2019 | Wixey et al. |
| 2019/0076142 | A1 | 3/2019 | Wixey |
| 2019/0076143 | A1 | 3/2019 | Smith |
| 2019/0099181 | A1* | 4/2019 | Shelton, IV ........... A61B 90/03 |
| 2019/0167266 | A1 | 6/2019 | Patel et al. |
| 2019/0200989 | A1 | 7/2019 | Burbank et al. |
| 2019/0239967 | A1 | 8/2019 | Ragosta et al. |
| 2019/0262088 | A1 | 8/2019 | Burbank |
| 2020/0138529 | A1 | 5/2020 | Ragosta et al. |
| 2020/0397430 | A1 | 12/2020 | Patel et al. |
| 2020/0405301 | A1 | 12/2020 | Shelton, IV et al. |
| 2021/0393340 | A1 | 12/2021 | Beckman et al. |
| 2021/0401433 | A1 | 12/2021 | Freidel et al. |

FOREIGN PATENT DOCUMENTS

| | | |
|---|---|---|
| WO | WO 2015/153642 A1 | 10/2015 |
| WO | WO 2017/083125 A1 | 5/2017 |
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,679, entitled "Powered Surgical Stapler Having Independently Operable Closure and Firing Systems," filed Aug. 16, 2021.
U.S. Appl. No. 17/402,695, entitled "Firing System Features for Surgical Stapler," filed Aug. 16, 2021.
U.S. Appl. No. 17/402,701, entitled "Multiple-Sensor Firing Lockout Mechanism for Powered Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,738, entitled "Firing Member Tracking Feature for Surgical Stapler," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,749, entitled "Firing Bailout System for Powered Surgical Stapler," filed Aug. 16, 2021.
U.S. Appl. No. 17/402,759, entitled "Deflectable Firing Member for Surgical Stapler," filed Aug. 16, 2021.
International Search Report and Written Opinion dated Dec. 2, 2022 for Application No. PCT/IB2022/057608, 13 pgs.

* cited by examiner

PROXIMALLY LOCATED FIRING LOCKOUT MECHANISM FOR SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
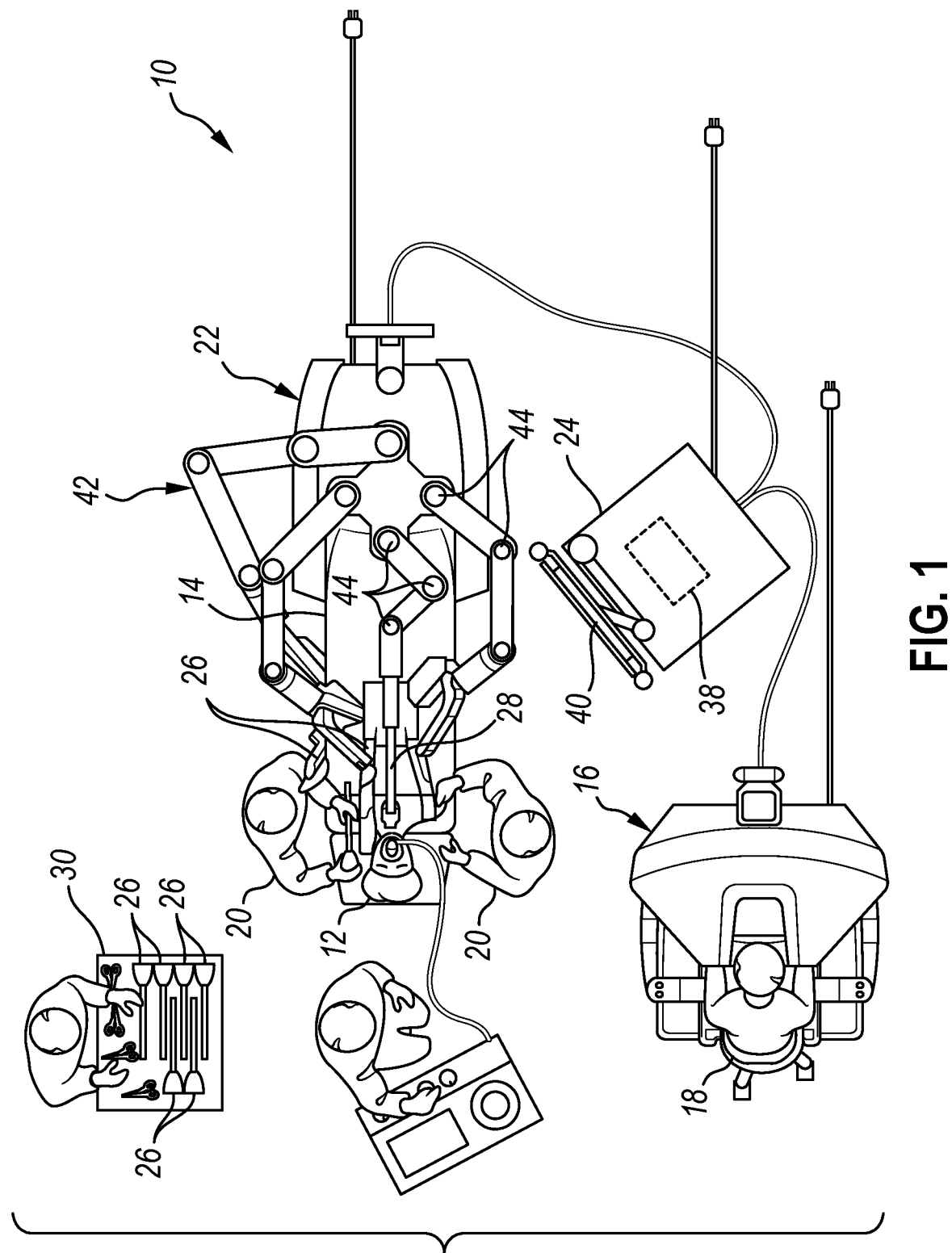
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018, issued as U.S. Pat. No. 11,076,926 on Aug. 3, 2021; U.S. Pub. No. 2018/0325606, entitled "Systems and Methods for Operating an End Effector," published Nov. 15, 2018, issued as U.S. Pat. No. 11,026,755 on Jun. 8, 2021; U.S. Pub. No. 2019/0200989, entitled "Stapler Reload Detection and Identification," published Jul. 4, 2019, issued as U.S. Pat. No. 11,364,029 on Jun. 21, 2022; U.S. Pub. No. 2019/0239967, entitled "Stapler Beam Architecture," published Aug. 8, 2019, issued as U.S. Pat. No. 11,166,773 on Nov. 9, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2019/0239877, entitled "Wrist Architecture," published Aug. 8, 2019, issued as U.S. Pat. No. 11,234,700 on Feb. 1, 2022; U.S. Pub. No. 2019/0201150, entitled "Push-Pull Surgical Instrument End Effector Actuation Using Flexible Tension Member," published Jul. 4, 2019, issued as U.S. Pat. No. 11,020,138 on Jun. 1, 2021; U.S. Pub. No. 2019/0282233, entitled "Stapler Cartridge With an Integral Knife," published Sep. 19, 2019, issued as U.S. Pat. No. 11,147,552 on Oct. 19, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2020/0138529, entitled "Locking System for Medical Device Drive System," published May 7, 2020, issued as U.S. Pat. No. 11,633,239 on Apr. 25, 2023; and/or U.S. Pub. No. 2020/0397430, entitled "Surgical Instrument With Lockout Mechanism," published Dec. 24, 2020, issued as U.S. Pat. No. 11,439,390 on Sep. 13, 2022. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
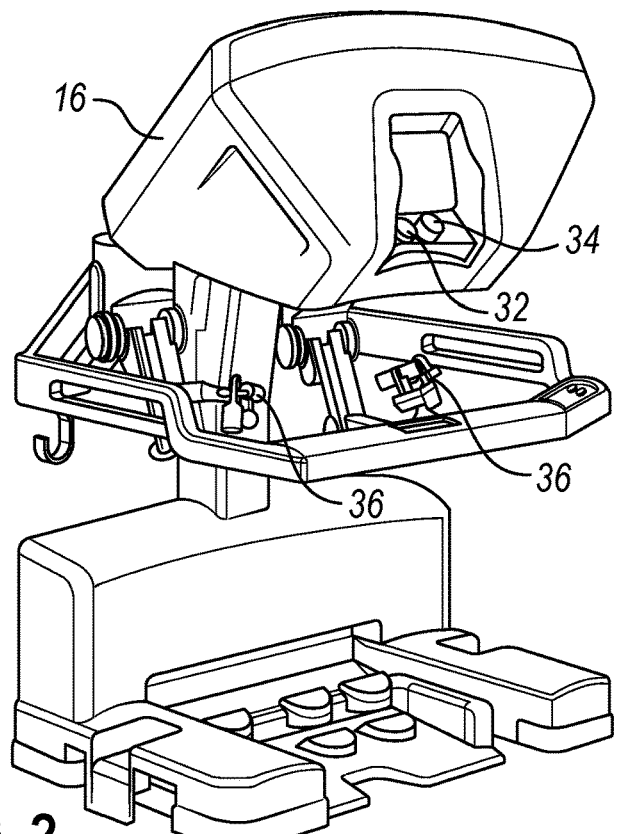
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
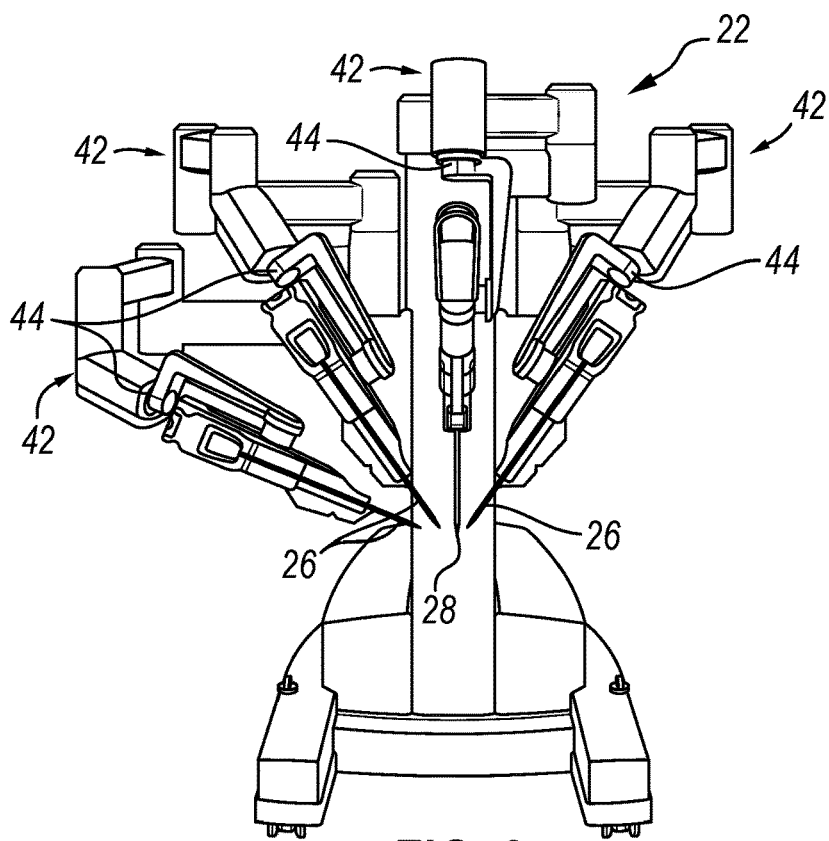
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
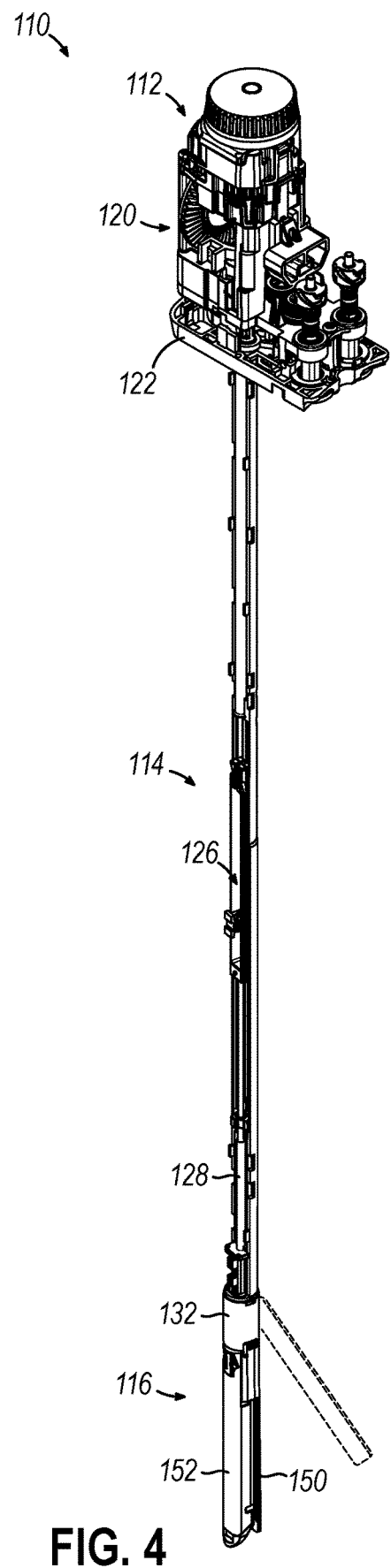
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
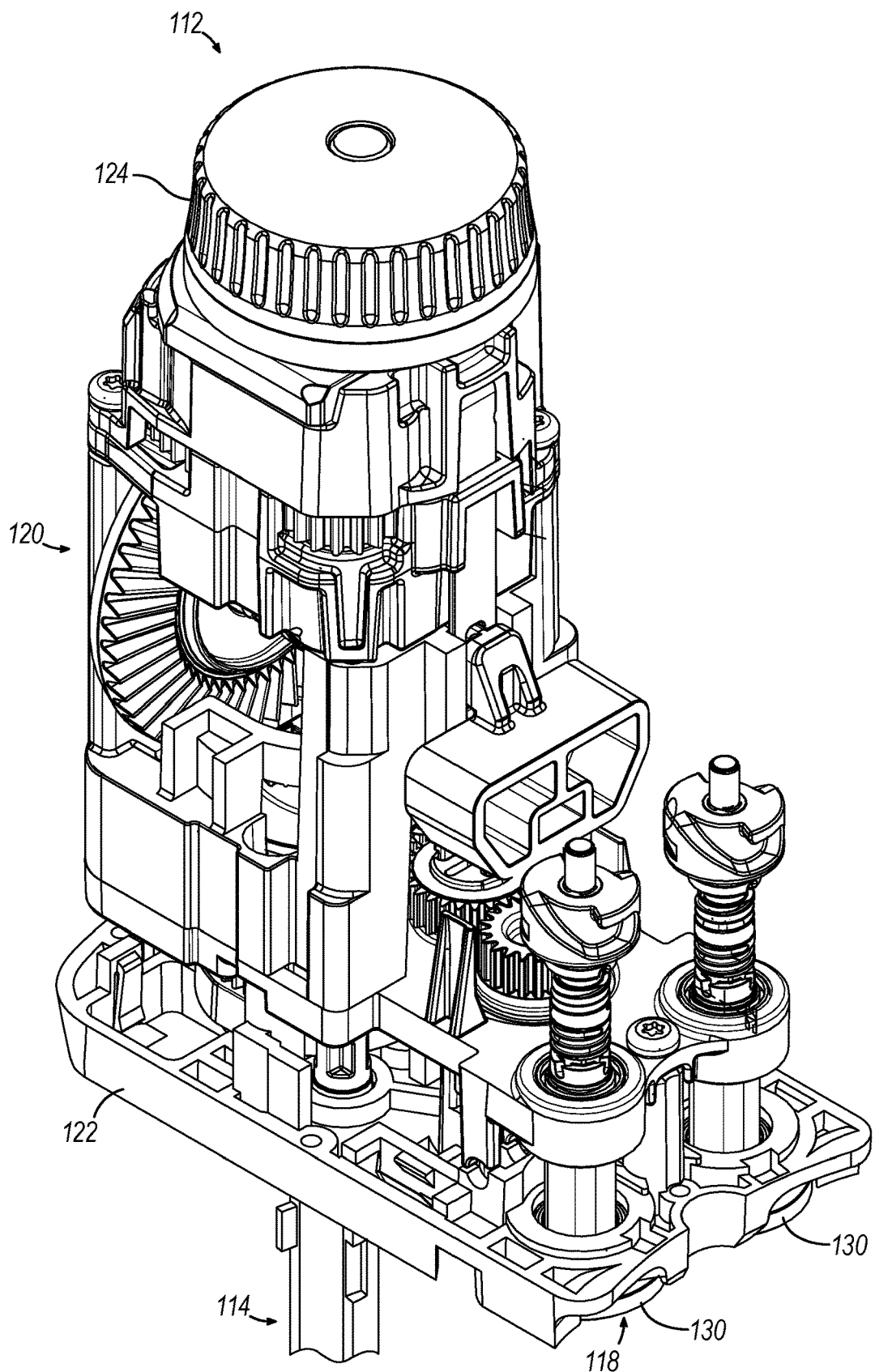
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). An articulation joint (132) is disposed between shaft assembly (114) and end effector (116). As shown in phantom lines in FIG. 4, in the articulated state the entirety of end effector (116) (including upper and lower jaws (150, 152)) extends at an angle relative to shaft assembly (114). As shown in solid lines in FIG. 4, in the non-articulated state, end effector (116) extends parallel with shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

Figure 6:
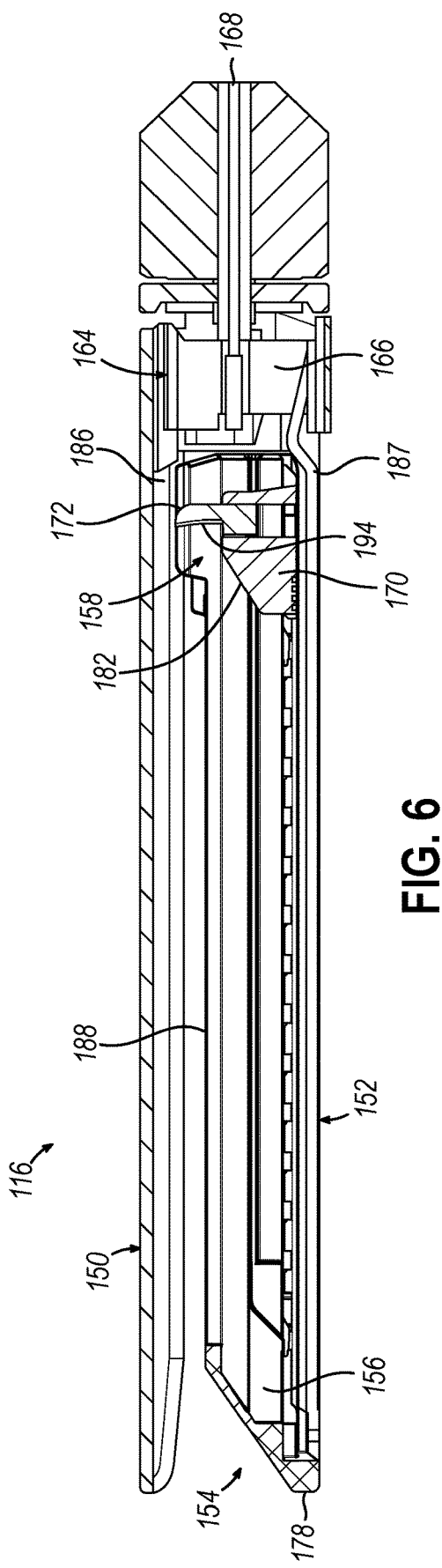
FIG. 6 depicts a side cross-sectional view of the end effector of FIG. 4, where the end effector includes a staple cartridge.

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
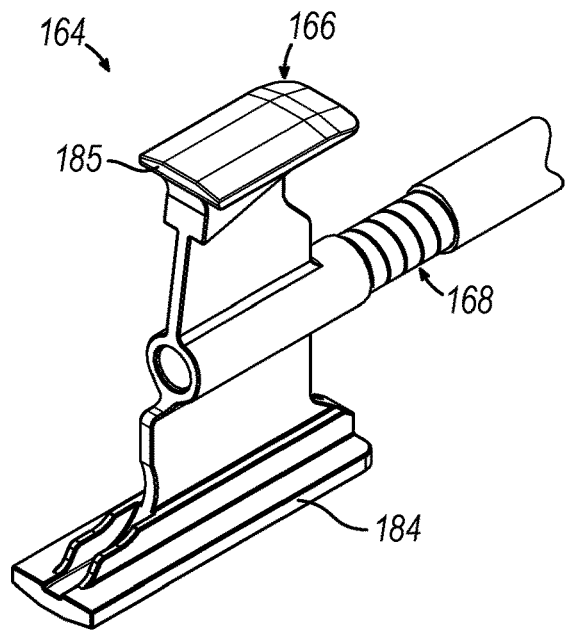
FIG. 8 depicts a perspective view of a driving assembly configured for use with the staple cartridge of FIG. 7.
Figure 9:
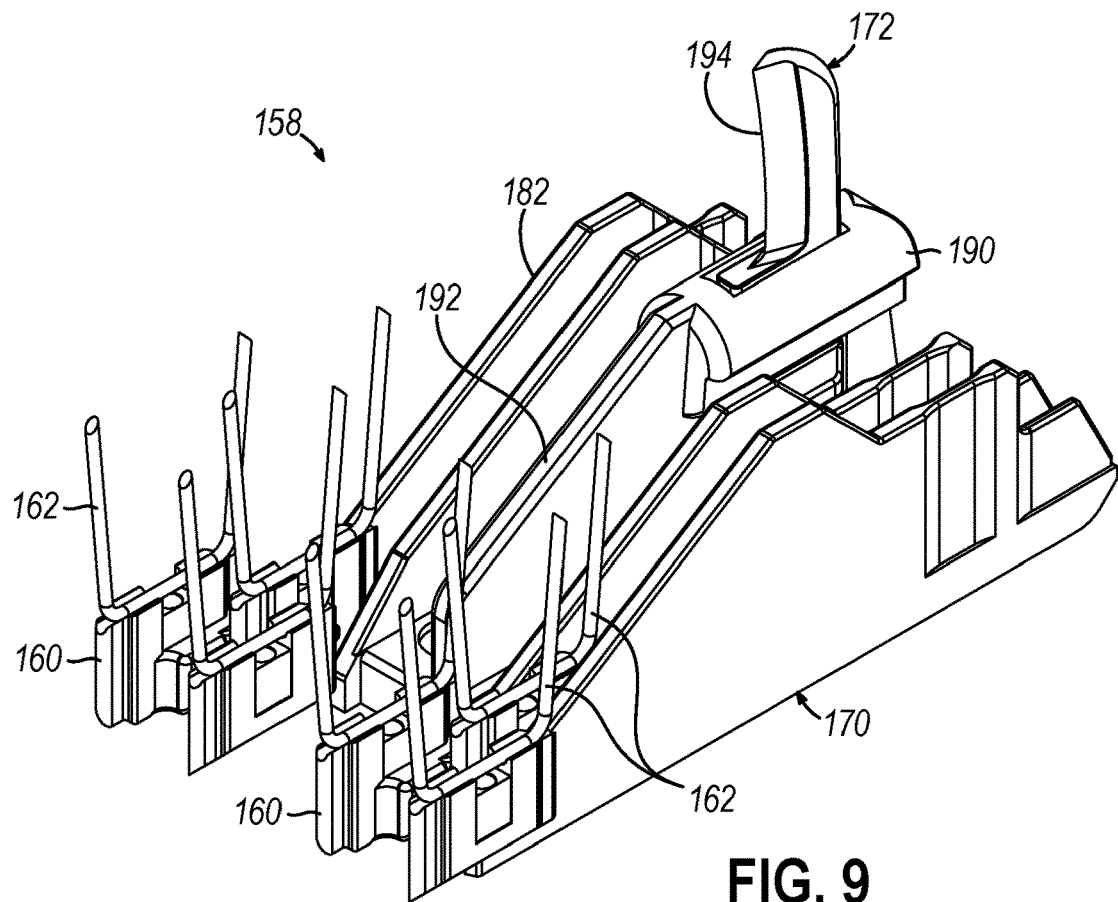
FIG. 9 depicts a perspective view of a knife assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

Figure 7:
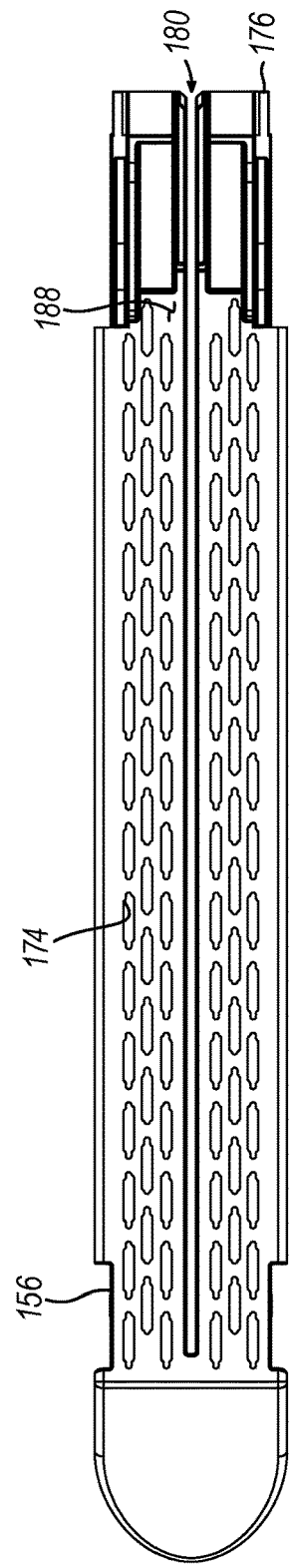
FIG. 7 depicts a top view of a deck of the staple cartridge of FIG. 6.

FIG. 7 shows a top view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end (176) of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
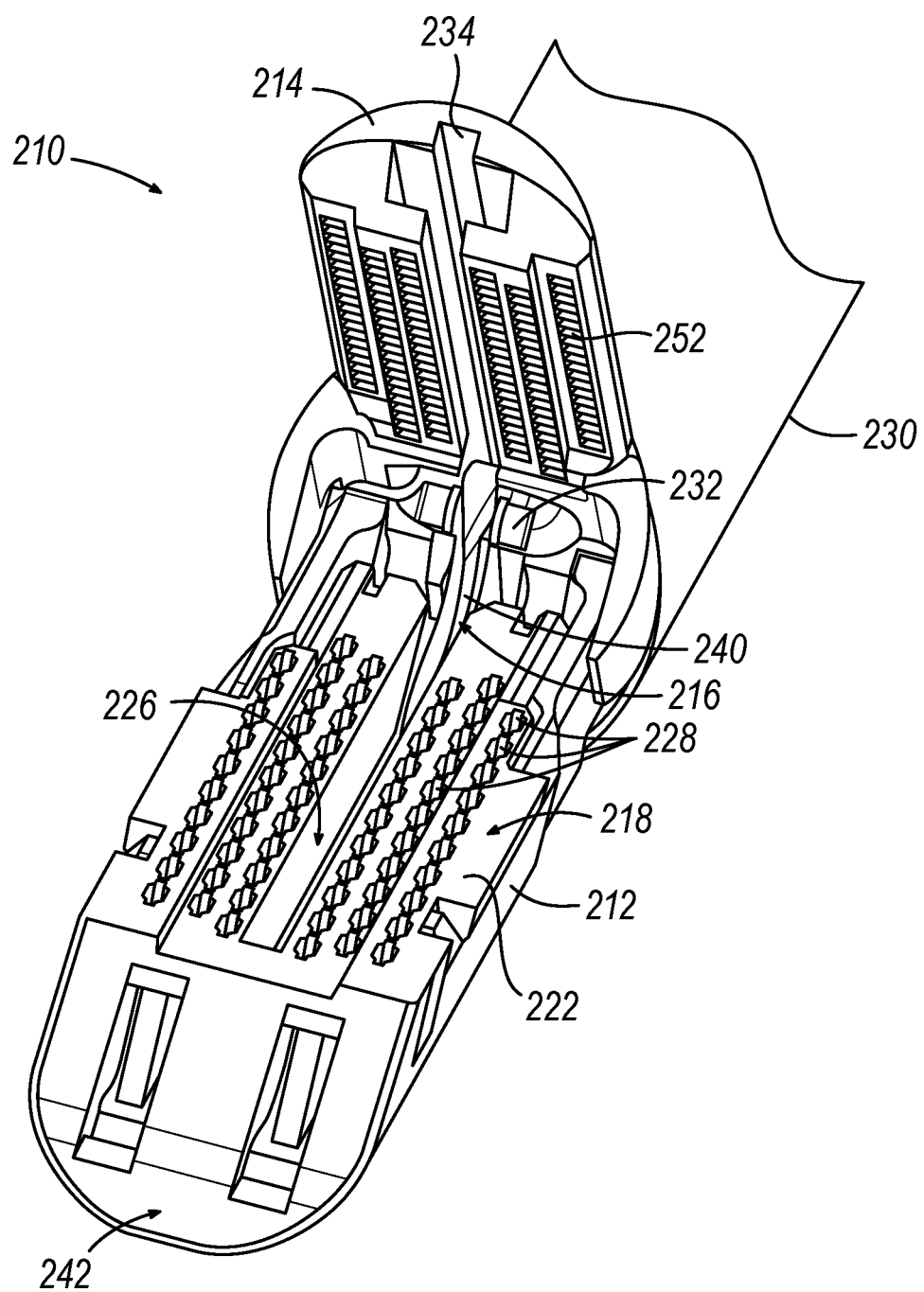
FIG. 10 depicts a perspective view of a second exemplary end effector that may be configured for use with the robotic surgical system of FIG. 1.
Figure 11:
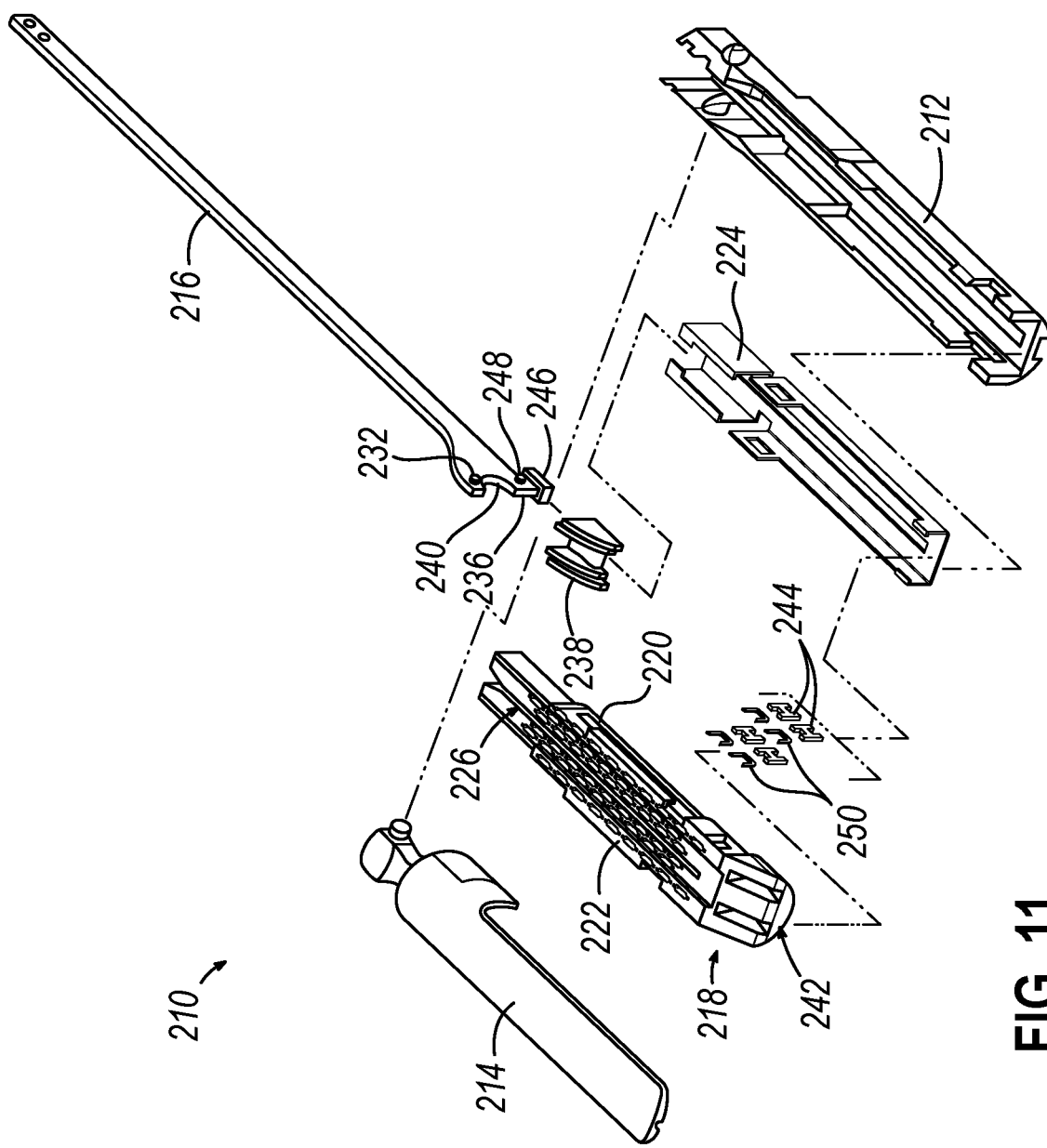
FIG. 11 depicts an exploded perspective view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, issued as U.S. Pat. No. 11,744,544 on Sep. 5, 2023, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, published as U.S. Pub. No. 2021/0393340 on Dec. 23, 2021, the disclosure of which is hereby incorporated by reference herein in its entirety.

It will be appreciated that any one or more of the teachings described below may be combined with any one or more of the teachings described above in connection with FIGS. 1-11.

II. Exemplary Firing Lockout Assembly for Surgical Instrument

In some instances, it may be desirable to provide surgical instrument (110) with a firing lockout assembly to prevent a firing member, such as push rod (168), from advancing when staple cartridge (154) is either absent, improperly installed, or already spent. For example, this may include when staple cartridge (154) is improperly installed within the channel of lower jaw (152) of end effector (116). Such prevention of distal actuation of pusher member (166) in the absence of a usable staple cartridge (154) may prevent inadvertent closing of end effector (116) which may otherwise occur via distal advancement of second flange (185) along longitudinal slot (187) of lower jaw (152); and/or may prevent inadvertent firing of end effector (116) which may otherwise occur via transmission of distal motion from pusher member (166) to wedge sled (170).

As will be described with reference to FIGS. 12-14C, surgical instrument (110) may include, amongst other components, end effector (116), an articulation joint (310), a shaft assembly (312), a firing system (314), and a firing lockout assembly (316). As previously described, surgical instrument (110) may be removably coupled with robotic arm (42) of robotic surgical system (10) using instrument base (112). As previously described with reference to FIGS. 4-5, instrument base (112) includes attachment interface (118) with input couplers (130) that are configured to interface with and be driven by corresponding output couplers (not shown) of robotic arm (42) of patient side cart (22). As previously described, end effector (116) includes upper and lower jaws (150, 152); however, use of end effector (210) is also envisioned. End effector (116, 210) is operatively coupled with shaft assembly (312).

Shaft assembly (312) extends distally from drive system (120) (see FIG. 4) and is similar to shaft assembly (114) described above except as otherwise described below. As shown, shaft assembly (312) includes a deflecting member (318) that may comprise a separate component of shaft assembly (312) or may be coupled with an outer housing (not shown) of shaft assembly (312). As will be described in greater detail with reference to FIGS. 14A-14C, deflecting member (318) may move relative to a lockout member (320) of firing lockout assembly (316) between locked and unlocked configurations.

Articulation joint (310) is similar to articulation joint (132) shown in FIG. 4, except as otherwise described below. Articulation joint (310) is disposed between shaft assembly (312) and end effector (116) similar to articulation joint (132). Articulation joint (310) is configured to rotate end effector (116) between an articulated state and a non-articulated state similar to articulation joint (132) (see FIG. 4).

Figure 12:
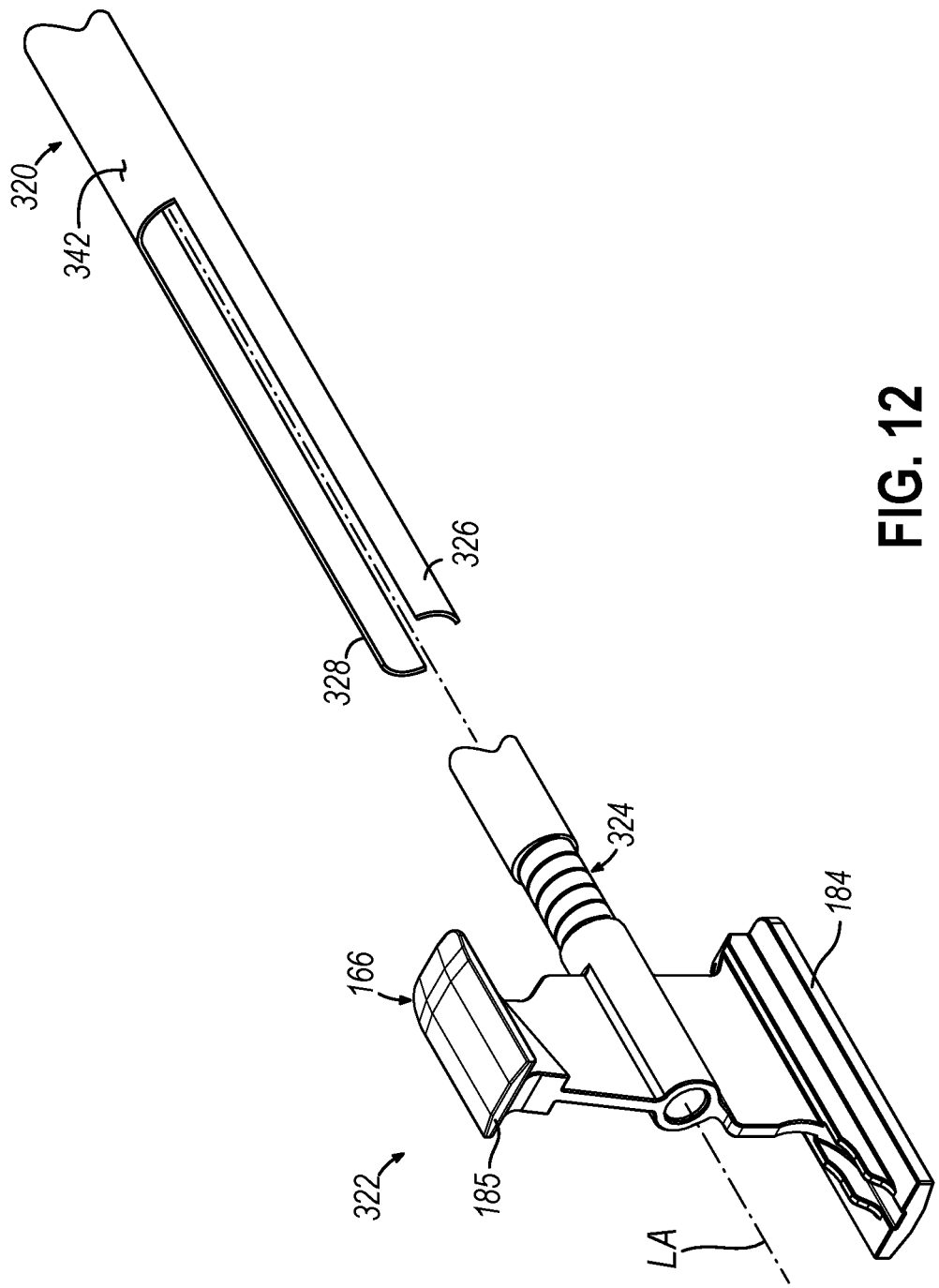
FIG. 12 depicts a partial exploded perspective view of a driving assembly similar to FIG. 8 and an exemplary lockout member of an exemplary firing lockout assembly.

Firing system (314) is operable to actuate end effector (116) from an open state (see FIG. 10) regarding end effector (210) to a closed state (see FIG. 4) regarding end effector (116). Firing system (314) extends through at least a portion of shaft assembly (312) and end effector (116). Firing system (314) is operable to at least cut and staple tissue once upper and lower jaws (150, 152) are in the closed state. Firing system (314) may be driven by an actuator either disposed within instrument base (112) or coupled with instrument base (112). Firing system (314) includes a driving assembly (322), similar to driving assembly (164), described above except as otherwise described below. FIG. 12 shows a partial exploded perspective view of driving assembly (322) and a distal portion of firing lockout assembly (316). Driving assembly (322) includes pusher member (166) and an elongate rod (e.g., a push rod (324) which may be similar to push rod (168)). Push rod (324) may extend within portions of shaft assembly (312) and end effector (116) along a longitudinal axis (LA) in the non-articulated state.

Firing lockout assembly (316) is selectively coupled with firing system (314). Firing lockout assembly (316) is configured to move between a locked configuration (see FIGS. 13A and 14A) and an unlocked configuration (see FIGS. 13B and 14B). Firing lockout assembly (316) may determine both a presence and a use status of staple cartridge (154) when staple cartridge (154) is inserted within a cartridge support channel of lower jaw (152). For example, firing lockout assembly (316) may be operable to inhibit actuation of firing system (314) to prevent repeated firing of end effector (116) when no staple cartridge (154) is present, when an already deployed staple cartridge (154) is inserted, or an incomplete coupling of staple cartridge (154) with lower jaw (152) occurs. In other words, firing lockout assembly (316) is configured to inhibit actuation of firing system (314) in the locked configuration in response to unspent usable staple cartridge (154) being absent from lower j aw (152). Firing lockout assembly (316) may sense proximal end (176) of staple cartridge body (156).

Figure 13A:
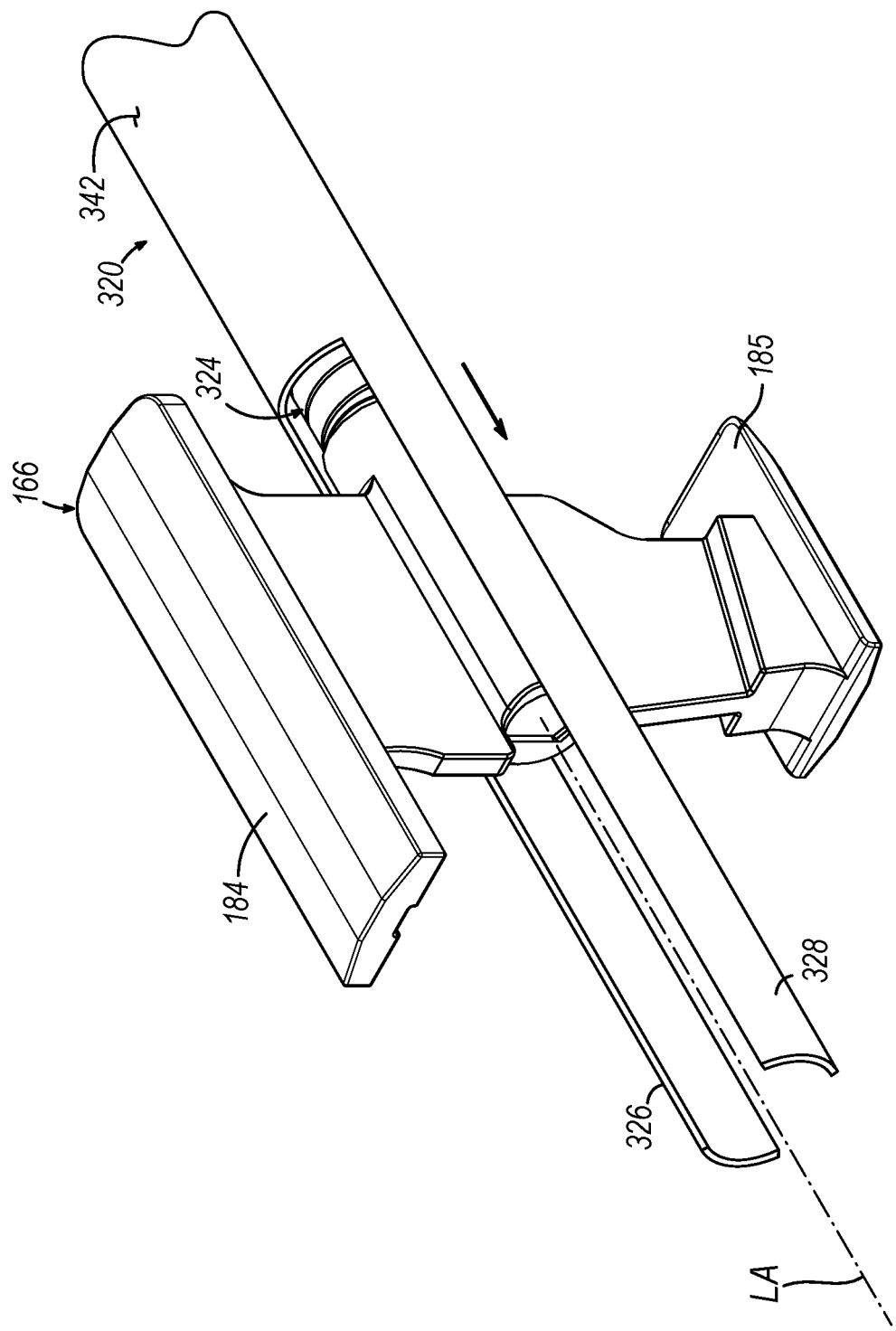
FIG. 13A depicts a perspective view of the driving assembly and the lockout member of FIG. 12 firing lockout assembly in a locked configuration.
Figure 13B:
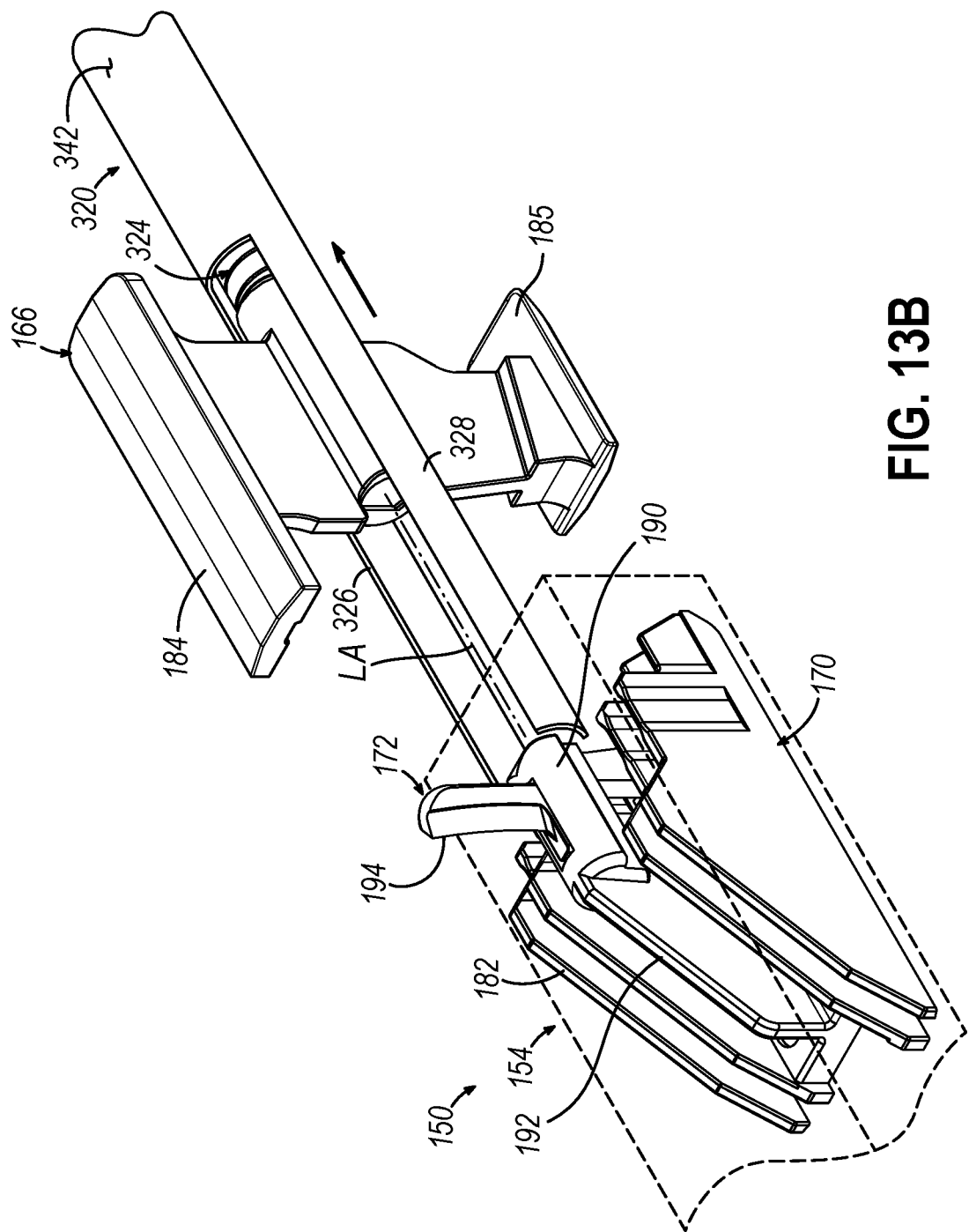
FIG. 13B depicts a perspective view of the driving assembly and the distal portion of the firing lockout assembly of FIG. 1, but with the firing lockout assembly in an unlocked configuration in the presence of the staple cartridge of FIG. 6.
Figure 14A:
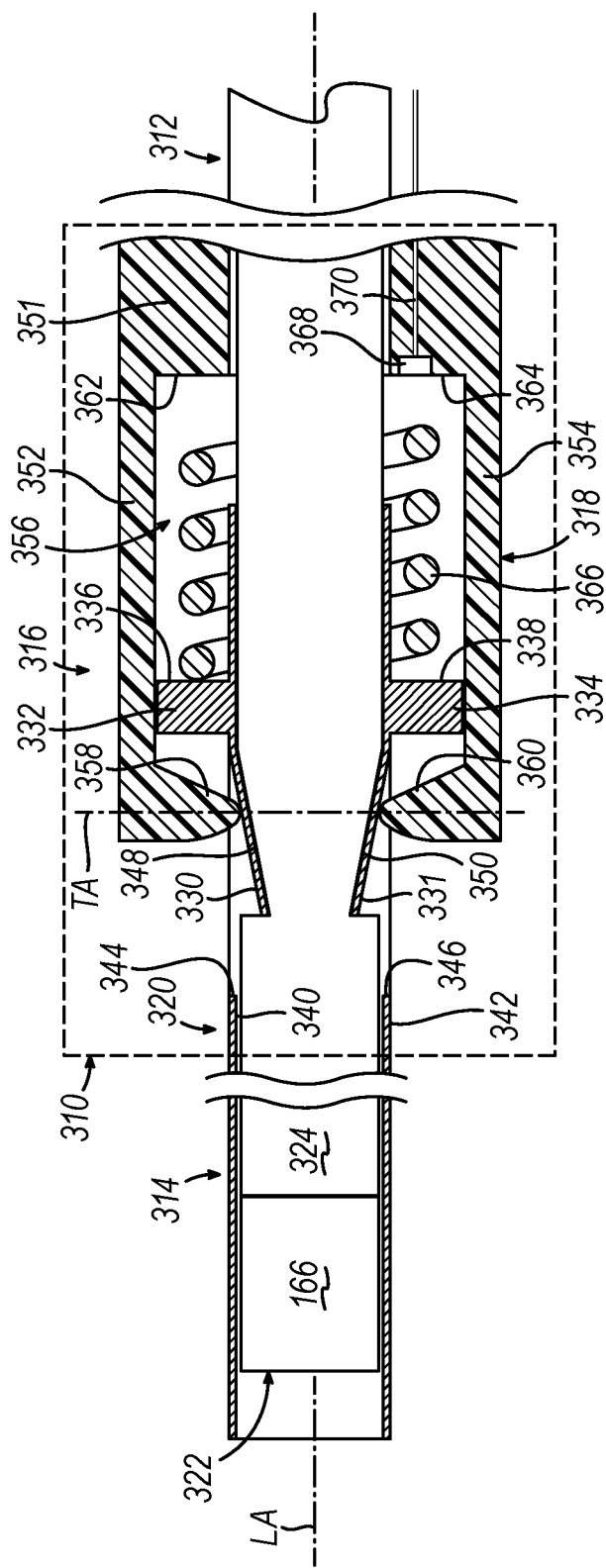
FIG. 14A depicts a schematic cross-sectional view of the firing lockout assembly disposed proximal to the end effector of FIG. 6, where the firing lockout assembly is in the locked configuration of FIG. 13A.

FIGS. 13A and 14A show firing lockout assembly (316) in the locked configuration. Particularly, FIG. 13A shows a perspective view of driving assembly (322) and a distal portion of firing lockout assembly (316) in the locked configuration, and FIG. 14A shows a schematic sectional view of firing lockout assembly (316) disposed proximal to end effector (116) of FIG. 6. Firing lockout assembly (316) includes lockout member (320) which is translatable at least through portions of articulation joint (310) or shaft assembly (312). Lockout member (320) is configured to translate from a first position to a second position in response to unspent staple cartridge (154) being received by lower jaw (152). Lockout member (320) extends into end effector (116) and has the ability to overcome the bias and unlock firing system (314). Lockout member (320) controls the distal translation of pusher member (166). Lockout member (320), which may be spring biased, communicates the location of wedge sled (170) or the presence of staple cartridge (154) to deflecting member (318) located proximal to the proximal end of vertical slot (180) of staple cartridge (154). As shown in FIGS. 13A-13B, lockout member (320) includes opposing first and second arms (326, 328).

As will be described in greater detail with reference to FIGS. 14A-14C, firing lockout assembly (316) is disposed proximal to end effector (116). As previously described, in some versions, firing lockout assembly (316) may be located within articulation joint (310). In this version, lockout member (320) may be supported in the firing member support member and lock into the flexible firing member. Alternatively, firing lockout assembly (316) may be located proximal to articulation joint (310) for example, at a proximal end of articulation joint (310). In this version, firing lockout assembly (316) may include a biasing element (e.g., a compression spring) that is supported within the tube support member and locks into the flexible support member proximally or with push rod (324).

As shown in FIG. 14A, lockout member (320) includes first and second deflectable portions (330, 331) that are configured to deflect about a transverse axis (TA) that extends transversely to longitudinal axis to inhibit actuation of firing system (314) while in the locked configuration. Lockout member (320) includes opposing first and second projections (332, 334) defining first and second contact surfaces (336, 338). Lockout member (320) includes inner and outer surfaces (340, 342). Lockout member (320) includes first and second cutout portions (344, 346) extending through inner and outer surfaces (340, 342) of lockout member (320). Inner surface (340) of lockout member (320) may surround at least a portion of push rod (324). Push rod (324) includes at least one recessed portion, with first and second recessed portions (348, 350) being shown. First and second recessed portions (348, 350) are configured to receive first and second deflectable portions (330, 331) of lockout member (320) to inhibit actuation of firing system (314) in the locked configuration of FIGS. 13A and 14A.

With continued reference to FIG. 14A, deflecting member (318) includes a body (351) with first and second arms (352, 354) disposed around outer surface (342) of lockout member (320) defining a cavity (356). A first rigid engagement feature (358) is disposed at the distal terminal end of first arm (352), and a second rigid engagement feature (360) is disposed at the distal terminal end of second arm (354). Deflecting member (318) includes first and second contact surfaces (362, 364). First and second rigid engagement features (358, 360) are configured to engage first and second deflectable portions (330, 331) of lockout member (320) in the locked configuration. Firing lockout assembly (316) includes a biasing element (shown as compression spring (366)) configured to bias lockout member (320) toward locked configuration. Compression spring (366) is disposed within cavity (356) between first and second contact surfaces (362, 364) of deflecting member (318) at a proximal end and between first and second contact surfaces (336, 338) of lockout member (320) at a distal end.

Figure 14B:
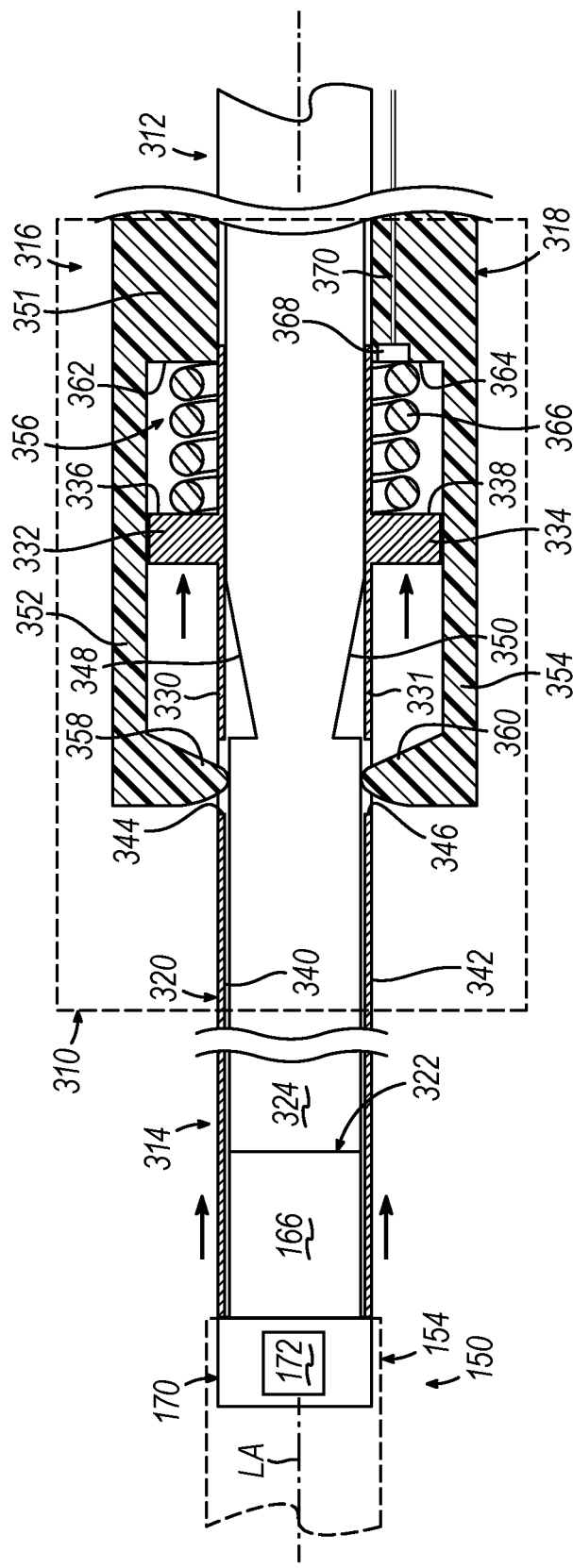
FIG. 14B depicts a schematic cross-sectional view of the firing lockout assembly and the end effector of FIG. 14A, but with the firing lockout assembly being moved to the unlocked configuration of FIG. 13B.
Figure 14C:
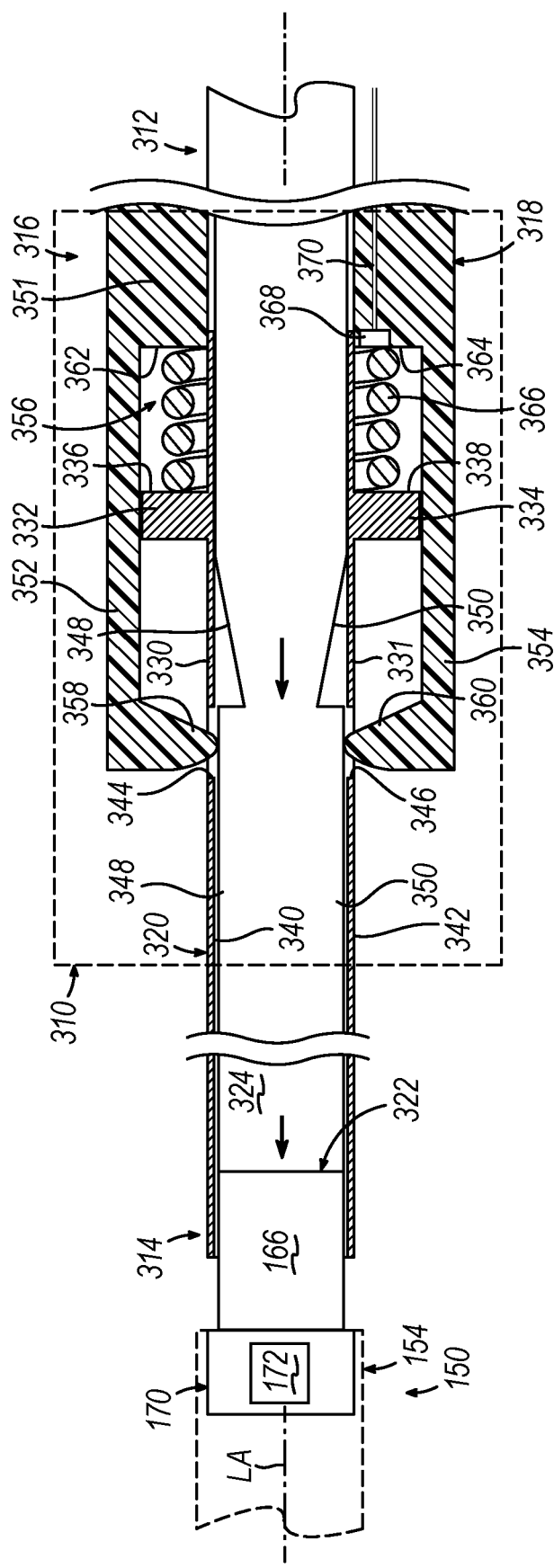
FIG. 14C depicts a schematic cross-sectional view of the firing lockout assembly and disposed proximal to the end effector of FIG. 14B, but with the driving assembly being driven distally to actuate the staple cartridge after the firing lockout assembly is moved to the unlocked configuration.

While FIGS. 14A-14C show first and second deflectable portions (330, 331), first and second projections (332, 334), first and second contact surfaces (336, 338), first and second cutout portions (344, 346), first and second recessed portions (348, 350), first and second arms (352, 354), first and second rigid engagement features (358, 360), and first and second contact surfaces (362, 364), it is envisioned that a single component/portion/surface may be incorporated for one or more of the component/portion/surface. For example, in some instances, an annular component/portion/surface may be incorporated.

FIGS. 13B and 14B show firing lockout assembly (316) moved to the unlocked configuration. Particularly, FIG. 13B shows a perspective view of the driving assembly (322) and lockout member (320) of firing lockout assembly (316) of FIG. 12 in the unlocked configuration in the presence of staple cartridge (154) of FIG. 6, and FIG. 14B shows a schematic sectional view of firing lockout assembly (316) and end effector (116) of FIG. 14A, but with firing lockout assembly (316) moved to the unlocked configuration of FIG. 13B. Firing lockout assembly (316) is configured to allow actuation of firing system (314) in the unlocked configuration in response to unspent staple cartridge (154) being coupled with second jaw. As shown in FIG. 14B, lockout member (320) is moved relative to deflecting member (318) as lockout member (320) moves from the locked configuration to the unlocked configuration.

Driving assembly (322) may contact lockout member (320) to force lockout member (320) to translate proximally. Particularly, guide member (190) of wedge sled (170) may contact first and second arms (352, 354) to translate lockout member (320) proximally which causes first and second deflectable portions (330, 331) to translate proximally and exit first and second recessed portions (348, 350) of push rod (324). This proximal movement of first and second deflectable portions (330, 331) also causes first and second deflectable portions (330, 331) to disengage from or reduce the interference with first and second rigid engagement features (358, 360). As shown, first and second rigid engagement features (358, 360) are disposed adjacent first and second cutout portions (344, 346) thereby moving firing lockout assembly (316) to the unlocked configuration. Proximal movement of lockout member (320) causes proximal movement of first and second projections (332, 334) to compress compression spring (366). Compression spring (366) is resiliently biased to a compressed state between contact surfaces of deflecting member (318) and lockout member (320) in the unlocked configuration. In other words, the force exerted by the proximal end of staple cartridge (154) on lockout member (320) exceeds the spring force of compression spring (366) in the compressed state causing lockout member (320) to move proximally. As a result of the movement of lockout member (320), firing lockout assembly (316) may sense the presence and absence of the proximal end of staple cartridge (154) within lower jaw (152) while being disposed proximal to end effector (116). Particularly, firing lockout assembly (316) may sense proximal end (176) of staple cartridge body (156).

FIG. 14C shows a schematic sectional view of firing lockout assembly (316) disposed proximal to end effector (116) of FIG. 14B. Since firing lockout assembly (316) is in the unlocked configuration, push rod (324) may be activated distally to cause driving assembly (322) to actuate staple cartridge (154). Optionally, first and second rigid engagement features (358, 360) may contact push rod (324) as push rod (324) translates.

As shown in FIGS. 14A-14C, firing lockout assembly (316) may include electrical lockout components in addition to mechanical lockout features. For example, in addition to or in place of the mechanical lockout provided by the interaction of deflecting member (318) and lockout member (320), an electrical signal continuity may be incorporated as a redundant safeguard to detect and provide feedback to the user and/or robotic surgical system (10) that that lockout member (320) is either in the locked or unlocked configuration. Electrical monitoring of one or more motors of robotic surgical system (10) may supplement the monitoring of firing lockout assembly (316). For example, firing lockout assembly (316) may include at least one electrical contact (368) disposed within firing lockout assembly (316) and configured to sense at least one of a presence or an absence of unspent staple cartridge (154). As previously described, robotic surgical system includes at least one actuator (e.g., a motor). Electrical contact (368) is configured to provide a signal wirelessly or using wire (370) to surgical instrument (110) in indicate the state of firing lockout assembly (316). As shown, electrical contact (368) is disposed adjacent second contact surface (364) of deflecting member (318); however, electrical contact (368) may be located in a variety of suitable positions.

Surgical instrument (110) is configured to prevent power to the motor in response to signal indicating that firing lockout assembly (316) is in the locked configuration. The signal received from electrical contact (368) may prevent power to the controlling motors. Lockout member (320) may be incapable of resisting the full force of pusher member (166) which is used cooperative with the monitoring of the torque or current of the motor which is related to the force experienced by knife member (172) and the location of knife member (172) to control advancement of the motor. If the limited force obstruction is detected in the stroke monitored zone, the motor may be deactivated preventing the firing of end effector (116).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a shaft assembly; (b) an end effector operatively coupled with the shaft assembly, wherein the end effector comprises: (i) a first jaw including an anvil, and (ii) a second jaw configured to removably receive an unspent staple cartridge, wherein at least one of the first or second jaws is configured to pivot relative to the other of the first or second jaws; (c) a firing system extending through at least a portion of the shaft assembly and the end effector, wherein the firing system is operable to staple and cut tissue; and (d) a firing lockout assembly selectively coupled with the firing system, wherein the firing lockout assembly is disposed proximal to the end effector, wherein the firing lockout assembly is configured to: (i) provide the firing system in an unlocked configuration to thereby allow actuation of the firing system in response to the unspent staple cartridge being coupled with the second jaw, and (ii) provide the firing system in a locked configuration to thereby inhibit actuation of the firing system in response to the unspent staple cartridge being absent from the second jaw.

Example 2

The surgical instrument of Example 1, further comprising an articulation joint disposed between the shaft assembly and the end effector, wherein the articulation joint is configured to transition the end effector between an articulated position and a non-articulated position.

Example 3

The surgical instrument of Example 2, wherein the firing lockout assembly is disposed within the articulation joint.

Example 4

The surgical instrument of any of Examples 2 through 3, wherein the firing lockout assembly is disposed proximal to the articulation joint within the shaft assembly.

Example 5

The surgical instrument of any of Examples 1 through 4, wherein the firing lockout assembly includes a lockout member configured to translate from a first position to a second position in response to the unspent staple cartridge being received by the second jaw.

Example 6

The surgical instrument of Example 5, wherein the firing system includes an elongate rod that extends along a longitudinal axis, wherein the lockout member includes a deflectable portion disposed proximal to the end effector and configured to deflect along a lateral axis to inhibit actuation of the firing system in the locked configuration, the lateral axis extending transversely to the longitudinal axis.

Example 7

The surgical instrument of Example 6, the elongate rod including at least one recessed portion disposed proximal to the end effector and configured to receive the deflectable portion of the lockout member to inhibit actuation of the firing system in the locked configuration.

Example 8

The surgical instrument of any of Examples 6 through 7, wherein the shaft assembly includes a deflecting member disposed proximal to the end effector, wherein the lockout member is configured to move relative to the deflecting member as the lockout member moves from the locked configuration to the unlocked configuration.

Example 9

The surgical instrument of Example 8, wherein the deflecting member includes a rigid engagement feature disposed proximal to the end effector and configured to engage the deflectable portion of the lockout member in the locked configuration.

Example 10

The surgical instrument of any of Examples 8 through 9, wherein the lockout assembly includes a biasing element disposed proximal to the end effector and configured to bias the lockout member toward the locked configuration.

Example 11

The surgical instrument of Example 10, wherein the deflecting member includes a contact surface, wherein the lockout member includes a projection defining a contact surface, wherein the biasing element is resiliently biased to a compressed state between the contact surfaces of the deflecting member and the lockout member in the unlocked configuration.

Example 12

The surgical instrument of any of Examples 1 through 11, wherein the firing lockout assembly includes at least one electrical contact disposed within the firing lockout assembly and configured to sense at least one of a presence or an absence of the unspent staple cartridge within the second jaw.

Example 13

The surgical instrument of Example 12, further comprising at least one motor, wherein the at least one electrical contact is configured to provide a signal to the surgical instrument that the firing lockout assembly is in the locked configuration, wherein the surgical instrument is configured to divert power to the motor in response to the signal indicating the firing lockout assembly is in the locked configuration.

Example 14

The surgical instrument of any of Examples 1 through 13, wherein the second jaw is configured to pivot relative to the first jaw between an open state for receiving the tissue and a closed state for clamping the tissue, wherein the firing system is operable to actuate the end effector from the open state to the closed state.

Example 15

The surgical instrument of any of Examples 1 through 14, wherein the unspent staple cartridge comprises: (i) a cartridge body defining a longitudinal axis and configured to be received by the second jaw, (ii) a plurality of staples housed within the cartridge body, (iii) a staple actuator translatable distally through the cartridge body along the longitudinal axis from an initial proximal position to a distal position, and (iv) a knife member translatably coupled with the staple actuator.

Example 16

A surgical instrument comprising: (a) a shaft assembly; (b) an end effector operatively coupled with the shaft assembly, wherein the end effector includes first and second jaws, wherein at least one of the first or second jaws is configured to pivot relative to the other of the first or second jaws, wherein the end effector is configured to removably receive a staple cartridge; (c) an articulation joint disposed between the shaft assembly and the end effector, wherein the articulation joint is configured to transition the end effector between an articulated position and a non-articulated position; (d) a firing system extending through at least a portion of the shaft assembly and the end effector, wherein the firing system is operable to drive the end effector to at least staple and cut tissue; and (e) a firing lockout assembly selectively coupled with the firing system, wherein the firing lockout assembly is disposed proximal to the end effector, wherein the firing lockout assembly is disposed within the articulation joint or proximal to the articulation joint within the shaft assembly, wherein the firing lockout assembly is configured to: (i) allow actuation of the firing system in an unlocked configuration in response to the staple cartridge being coupled with the end effector, and (ii) inhibit actuation of the firing system in a locked configuration in response to the staple cartridge being absent from the end effector.

Example 17

The surgical instrument of Example 16, wherein the firing lockout assembly includes a lockout member configured to translate from a first position to a second position in response to the staple cartridge being received by the end effector.

Example 18

The surgical instrument of Example 17, wherein the firing system includes an elongate rod that extends along a longitudinal axis, wherein the lockout member includes a deflectable portion that is configured to deflect along a lateral axis that extends transversely to the longitudinal axis to inhibit actuation of the firing system in the locked configuration.

Example 19

A robotic surgical system comprising: (a) a robotic arm; and (b) a surgical instrument configured to be removably coupled with the robotic arm, the surgical instrument comprising: (i) a shaft assembly, (ii) an end effector operatively coupled with the shaft assembly, wherein the end effector comprises: (A) a first jaw including an anvil, and (B) a second jaw configured to removably receive an unspent staple cartridge, wherein at least one of the first or second jaws is configured to pivot relative to the other of the first or second jaws, and (iii) a firing system extending through at least a portion of the shaft assembly and the end effector, wherein the firing assembly is operable to at least staple and cut tissue, and (iv) a firing lockout assembly selectively coupled with the firing system, wherein the firing lockout assembly is disposed proximal to the end effector, wherein the firing lockout assembly is configured to: (A) allow actuation of the firing system in an unlocked configuration in response to the unspent staple cartridge being coupled with the second jaw, and (B) inhibit actuation of the firing system in a locked configuration in response to the unspent staple cartridge being absent from the second jaw.

Example 20

The robotic surgical system of Example 19, wherein the firing lockout assembly includes at least one electrical contact disposed within the firing lockout assembly and configured to sense at least one of the presence or absence of the unspent staple cartridge.

IV. Miscellaneous

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, date herewith, published as U.S. Pub. No. 2023/0051361 on Feb. 16, 2023; U.S. patent application Ser. No. 17/402,675, entitled "Multi-Threshold Motor Control Algorithm for Powered Surgical Stapler," filed on Aug. 16, 2021, published as U.S. Pub. No. 2023/0051271 on Feb. 16, 2023; U.S. patent application Ser. No. 17/402,677, entitled "Variable Response Motor Control Algorithm for Powered Surgical Stapler," filed on Aug. 16, 2021, published as U.S. Pub. No. 2023/0048444 on Feb. 16, 2023; U.S. patent application Ser. No. 17/402,679, entitled "Powered Surgical Stapler Having Independently Operable Closure and Firing Systems," filed on Aug. 16, 2021, published as U.S. Pub. No. 2023/0051756 on Feb. 16, 2023 issued as U.S. Pat. No. 11,779,332 on Feb. 16, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,701, entitled "Multiple-Sensor Firing Lockout Mechanism for Powered Surgical Stapler," filed on Aug. 16, 2021, published as U.S. Pub. No. 2023/0050358 on Feb. 16, 2023; U.S. patent application Ser. No. 17/402,720, entitled "Cartridge-Based Firing Lockout Mechanism for Surgical Stapler," filed on Aug. 16, 2021, published as U.S. Pub. No. 2023/0051222 on Feb. 16, 2023; U.S. patent application Ser. No. 17/402,732, entitled "Multi-position Restraining Member for Sled Movement," filed on Aug. 16, 2021, published as U.S. Pub. No. 2023/0045893 on Feb. 16, 2023; U.S. patent application Ser. No. 17/402,738, entitled "Firing Member Tracking Feature for Surgical Stapler," filed on Aug. 16, 2021, published as U.S. Pub. No. 2023/0049736 on Feb. 16, 2023; U.S. patent application Ser. No. 17/402,744, entitled "Adjustable Power Transmission Mechanism for Powered Surgical Stapler," filed on Aug. 16, 2021, published as U.S. Pub. No. 2023/0051938 on Feb. 16, 2023; U.S. patent application Ser. No. 17/402,749, entitled "Firing Bailout System for Powered Surgical Stapler," filed on Aug. 16, 2021, published as U.S. Pub. No. 2023/0045998 on Feb. 16, 2023; and/or U.S. patent application Ser. No. 17/402,759, entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
(a) a shaft assembly;
(b) an end effector operatively coupled with the shaft assembly, wherein the end effector comprises:
(i) a first jaw including an anvil, and
(ii) a second jaw configured to removably receive an unspent staple cartridge, wherein at least one of the first or second jaws is configured to pivot relative to the other of the first or second jaws;
(c) a firing system extending along a longitudinal axis through at least a portion of the shaft assembly and the end effector, wherein the firing system is operable to staple and cut tissue; and
(d) a firing lockout assembly selectively coupled with the firing system, wherein the firing lockout assembly is disposed proximal to the end effector, wherein the firing lockout assembly is configured to:
(i) provide the firing system in an unlocked configuration to thereby allow actuation of the firing system in response to the unspent staple cartridge being coupled with the second jaw, and
(ii) provide the firing system in a locked configuration to thereby inhibit actuation of the firing system in response to the unspent staple cartridge being absent from the second jaw,
wherein the firing lockout assembly includes a first engagement projection and a lockout, wherein the lockout includes a first flexible deflectable portion disposed proximal to the end effector, wherein the first engagement projection is configured to push the first flexible deflectable portion inwardly toward the longitudinal axis to inhibit actuation of the firing system in the locked configuration.

2. The surgical instrument of claim 1, further comprising an articulation joint disposed between the shaft assembly and the end effector, wherein the articulation joint is configured to transition the end effector between an articulated position and a non-articulated position.

3. The surgical instrument of claim 2, wherein the firing lockout assembly is disposed within the articulation joint.

4. The surgical instrument of claim 1, wherein the lockout is configured to translate from a first position to a second position in response to the unspent staple cartridge being received by the second jaw.

5. The surgical instrument of claim 4, wherein the firing system includes an elongate rod that extends along the longitudinal axis, wherein the first flexible deflectable portion is configured to deflect along a lateral axis to inhibit actuation of the firing system in the locked configuration, the lateral axis extending transversely to the longitudinal axis.

6. The surgical instrument of claim 5, the elongate rod including at least one recessed portion disposed proximal to the end effector and configured to receive the first flexible deflectable portion of the lockout to inhibit actuation of the firing system in the locked configuration.

7. The surgical instrument of claim 5, wherein the shaft assembly includes a deflecting member disposed proximal to the end effector, wherein the deflecting member includes the first engagement projection, wherein the lockout is configured to move relative to the deflecting member as the lockout moves from the locked configuration to the unlocked configuration.

8. The surgical instrument of claim 7, wherein the first engagement projection is a a rigid engagement projection disposed proximal to the end effector and configured to engage the first flexible deflectable portion of the lockout in the locked configuration.

9. The surgical instrument of claim 7, wherein the lockout assembly includes a biasing element disposed proximal to the end effector and configured to bias the lockout toward the locked configuration.

10. The surgical instrument of claim 9, wherein the deflecting member includes a contact surface, wherein the lockout includes a projection defining a contact surface, wherein the biasing element is resiliently biased to a compressed state between the contact surfaces of the deflecting member and the lockout in the unlocked configuration.

11. The surgical instrument of claim 1, wherein the firing lockout assembly includes at least one electrical contact disposed within the firing lockout assembly and configured to sense at least one of a presence or an absence of the unspent staple cartridge within the second jaw.

12. The surgical instrument of claim 11, wherein the at least one electrical contact is configured to provide a signal to the surgical instrument that the firing lockout assembly is in the locked configuration, wherein the surgical instrument is configured to prevent power to a motor in response to the signal indicating the firing lockout assembly is in the locked configuration.

13. The surgical instrument of claim 1, wherein the second jaw is configured to pivot relative to the first jaw between an open state for receiving the tissue and a closed state for clamping the tissue, wherein the firing system is operable to actuate the end effector from the open state to the closed state.

14. The surgical instrument of claim 1, wherein the unspent staple cartridge comprises:
(i) a cartridge body configured to be received by the second jaw,
(ii) a plurality of staples housed within the cartridge body,
(iii) a staple actuator translatable distally through the cartridge body along the longitudinal axis from an initial proximal position to a distal position, and
(iv) a knife member translatably coupled with the staple actuator.

15. The surgical instrument of claim 1, wherein the firing lockout assembly includes a second engagement projection disposed opposite the first engagement projection, wherein the lockout includes a second flexible deflectable portion disposed proximal to the end effector, wherein the second engagement projection is configured to bend the second flexible deflectable portion inwardly toward the longitudinal axis to inhibit actuation of the firing system in the locked configuration.

16. A surgical instrument comprising:
(a) a shaft assembly;
(b) an end effector operatively coupled with the shaft assembly, wherein the end effector includes first and second jaws, wherein at least one of the first or second jaws is configured to pivot relative to the other of the first or second jaws, wherein the end effector is configured to removably receive a staple cartridge;
(c) an articulation joint disposed between the shaft assembly and the end effector, wherein the articulation joint is configured to transition the end effector between an articulated position and a non-articulated position;
(d) a firing system extending through at least a portion of the shaft assembly and the end effector, wherein the firing system is operable to drive the end effector to at least staple and cut tissue; and
(e) a firing lockout assembly selectively coupled with the firing system, wherein the firing lockout assembly includes at least one electrical contact configured to sense at least one of a presence or an absence of the staple cartridge within the second jaw, wherein the firing lockout assembly including the at least one electrical contact is disposed within the articulation joint or proximal to the articulation joint within the shaft assembly, wherein the firing lockout assembly is configured to:
(i) allow actuation of the firing system in an unlocked configuration in response to the staple cartridge being coupled with the end effector, and
(ii) inhibit actuation of the firing system in a locked configuration in response to the staple cartridge being absent from the end effector.

17. The surgical instrument of claim 16, wherein the firing lockout assembly includes a lockout configured to translate from a first position to a second position in response to the staple cartridge being received by the end effector.

18. The surgical instrument of claim 17, wherein the firing system includes an elongate rod that extends along a longitudinal axis, wherein the lockout includes a deflectable portion disposed proximal to the end effector and configured to deflect along a lateral axis that extends transversely to the longitudinal axis to inhibit actuation of the firing system in the locked configuration.

19. A robotic surgical system comprising:
(a) a robotic arm; and
(b) a surgical instrument configured to be removably coupled with the robotic arm, the surgical instrument comprising:
(i) a shaft assembly,
(ii) an end effector operatively coupled with the shaft assembly,
wherein the end effector comprises:
(A) a first jaw including an anvil, and
(B) a second jaw configured to removably receive an unspent staple cartridge, wherein at least on of the first or second jaws is configured to pivot relative to the other of the first or second jaws, (iii) a firing system extending along a longitudinal axis through at least a portion of the shaft assembly and the end effector, wherein the firing assembly is operable to at least staple and cut tissue, and (iv) a firing lockout assembly selectively coupled with the firing system, wherein the firing lockout assembly is disposed proximal to the end effector, wherein the firing lockout assembly is configured to:

(A) allow actuation of the firing system in an unlocked configuration in response to the unspent staple cartridge being coupled with the second jaw, and (B) inhibit actuation of the firing system in a locked configuration in response to the unspent staple cartridge bring absent from the second jaw, wherein the firing lock assembly includes a first engagement projection and a lockout, wherein the lockout is configured to translate along the longitudinal axis between the unlocked configuration and the locked configuration, wherein the lockout includes a first flexible deflectable portion disposed proximal to the end effector, and wherein the first engagement projection is configured to inwardly bend the first flexible deflectable portion toward the longitudinal axis to inhibit actuation of the firing system in the locked configuration.

* * * * *